United States Patent [19]
Rabenau et al.

[11] Patent Number: 5,344,292
[45] Date of Patent: Sep. 6, 1994

[54] FLUID PUMPING SYSTEM AND APPARATUS

[75] Inventors: Richard Rabenau, Birmingham; Stephen P. Lisak; Terry B. Kehne, both of Arab, all of Ala.

[73] Assignee: Ryder International Corporation, Arab, Ala.

[21] Appl. No.: 932,752

[22] Filed: Aug. 20, 1992

[51] Int. Cl.$^5$ ............................................. F04B 43/02
[52] U.S. Cl. .................................. 417/413 R; 604/153; 417/540; 417/360
[58] Field of Search ................ 417/394, 395, 383–388, 417/360, 413; 604/153, 113

[56] References Cited

U.S. PATENT DOCUMENTS

| | | | |
|---|---|---|---|
| 4,303,376 | 12/1981 | Siekmann | 417/384 |
| 4,411,603 | 10/1983 | Kell | 417/479 |
| 4,479,760 | 10/1984 | Bilstad et al. | 417/395 |
| 4,479,761 | 10/1984 | Bilstad et al. | 604/153 |
| 4,573,883 | 3/1986 | Noon et al. | 417/394 |
| 4,758,238 | 7/1988 | Sundblom et al. | 604/153 |
| 4,818,186 | 4/1989 | Pastrone et al. | 417/413 |
| 4,898,584 | 2/1990 | Borsanyi et al. | 604/153 |
| 4,983,102 | 1/1991 | Swain | 417/394 |
| 5,098,262 | 3/1992 | Wecker et al. | 604/153 |

Primary Examiner—Richard A. Bertsch
Assistant Examiner—Peter Korytnyk
Attorney, Agent, or Firm—Trexler, Bushnell, Giangiorgi & Blackstone, Ltd.

[57] ABSTRACT

A fluid pumping assembly for particular use in delivery of sterile fluid used in surgical procedures, includes a pump control structure to which a replaceable fluid pumping cartridge is connected and disconnected to provide convenient replacement and disposability of the cartridge. The pump cartridge is self-contained in that it includes a fluid pump which is adapted for automatic connection to a pump drive structure when the cartridge is inserted into the assembly, so that the sterile fluid is pumped only through the pumping cartridge and fluid flow is entirely isolated from the pump control structure to ensure that the fluid is maintained sterile during pumping. The cartridge can include a selectively activated pulsation control to enable discharging the fluid from the cartridge in either a continuous flow or pulsating flow of the fluid. The pump control structure can provide a pneumatic drive system which cycles pressurized air to drive the pump. A pneumatic control valve provides cycled switching of alternating air pressure and exhaust communication with the pump.

39 Claims, 6 Drawing Sheets

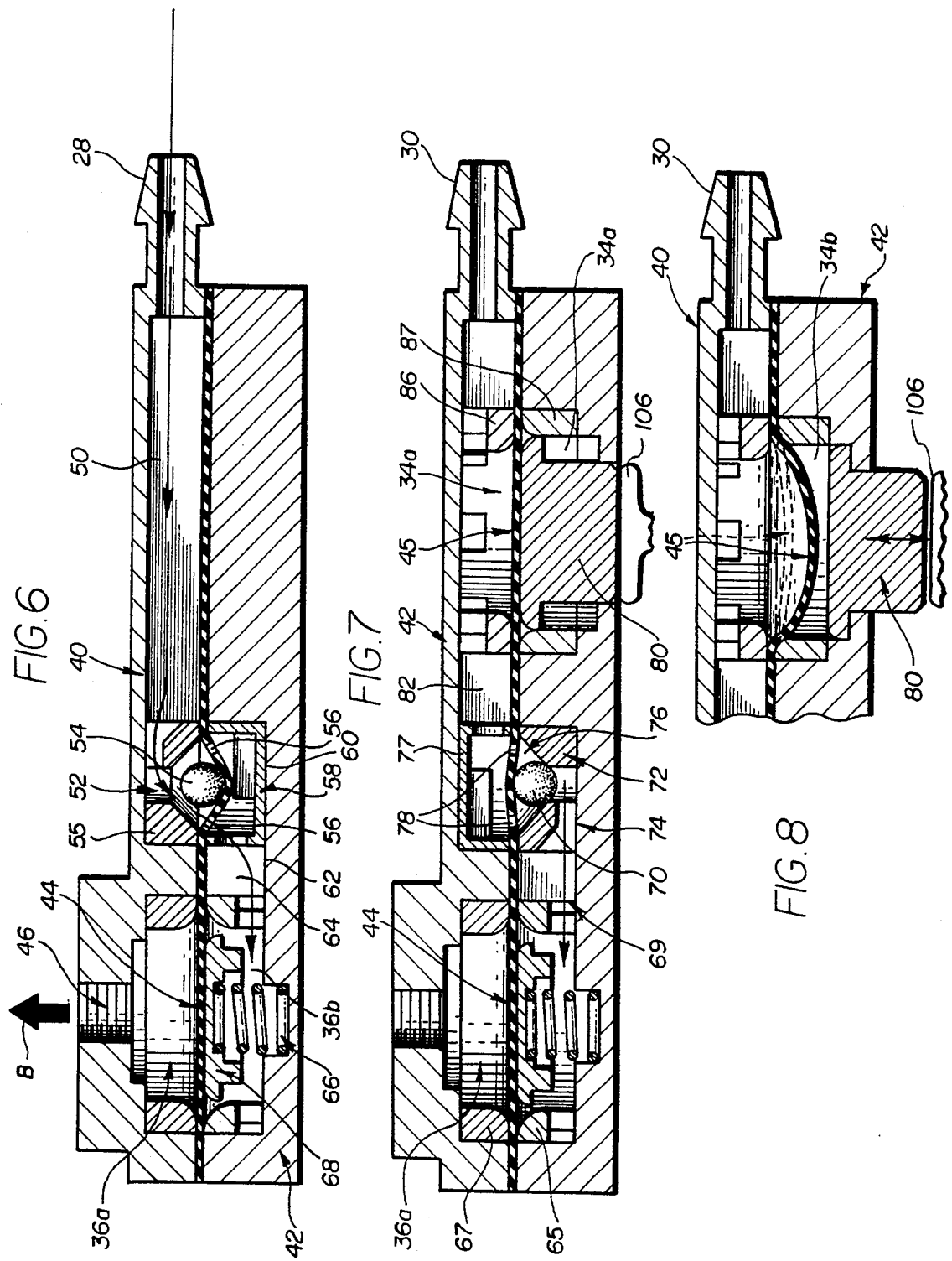

PRESSURIZED (AIR FLOW IN)
EXHAUSTED (AIR FLOW OUT)

5,344,292

FLUID PUMPING SYSTEM AND APPARATUS

BACKGROUND OF THE INVENTION

This invention relates to fluid pump systems, and more particularly relates to improved fluid delivery apparatus adapted for use in surgical procedures to deliver a continuous supply of sterile fluid, wherein a replaceable pump cartridge is employed.

In surgical procedures, particularly laparoscopic procedures, irrigation solution, typically sterile saline is directed under pressure to irrigate the surgical site. In order to ensure the sterile condition of the pressurized fluid, the fluid pump and delivery systems must also be in sterile condition which has required the effort and attention of skilled personnel to prepare sterilized equipment, and to sterilize the pumping apparatus preparatory to each procedure.

In addition, the surgeon often prefers to employ a pulsating stream of the pressurized irrigation fluid, for example, to facilitate disintegration of clots or dislodgement of severed tissue. Heretofore, irrigation pumping units have been limited to either a continuous irrigation stream or a pulsating stream, requiring use of multiple equipment to accommodate choice of irrigation stream condition. These disadvantages are eliminated by the system and apparatus in accordance with the present invention.

SUMMARY OF THE INVENTION

According to the present invention, a fluid pumping assembly for particular use in delivery of sterile fluid used in surgical procedures, includes a pump control structure to which a replaceable fluid pumping cartridge is connected and disconnected to provide convenient replacement and disposability of the cartridge. The pump cartridge is self-contained in that it includes a fluid pump which is adapted for automatic connection to a pump drive structure when the cartridge is inserted into the assembly, so that the sterile fluid is pumped only through the pumping cartridge and fluid flow is entirely isolated from the pump control structure to ensure that the fluid is maintained sterile during pumping. The pump cartridge is easily replaceable, and can be disposed of following a surgical procedure. Thus, since only the pump cartridge is in contact with the sterile saline, or the like, there is no need to sterilize the apparatus between procedures.

In one embodiment, the cartridge includes a selectively activated pulsation control to enable discharging the fluid from the cartridge in either a continuous flow or pulsating flow of the fluid. The cartridge can be constructed with a split housing which clamps a resilient diaphragm integrally including one diaphragm portion which oscillates to pump the fluid and another diaphragm portion which forms one wall of an accumulator chamber which can selectively, elastically absorb pressure pulses from the oscillating pump and modulate the pulses into continuous flow.

The pump control structure can provide a pneumatic drive system which cycles pressurized air to drive oscillation of the pump diaphragm. A pneumatic control valve provides cycled switching of alternating air pressure and exhaust communication with the diaphragm. The control valve can be adjustably piloted to enable variable frequency of the cycled air pressure drive and the pump diaphragm oscillation.

BRIEF DESCRIPTION OF THE DRAWINGS

FIG. 4 is a sectional view of the cartridge taken along a plane indicated by line 4—4 in FIG. 2;

FIG. 5 is a sectional view of the cartridge taken along a plane indicated by line 5—5 in FIG. 2, and illustrating pressurized fluid discharge from the cartridge with completion of a pumping portion of the cycled pump action within the cartridge;

FIG. 6 is a sectional view of the cartridge taken along a plane indicated by line 6—6 in FIG. 2, illustrating fluid drawn into the cartridge with the return portion of the cycled pumping action;

FIG. 7 is a sectional view taken along a plane indicated by line 7—7 in FIG. 2, and illustrating interrupted flow in pulsating flow operation of the cartridge;

FIG. 8 is a fragmentary sectional view of the accumulator chamber shown in FIG. 7 and showing the selective operation of the accumulator chamber to enable continuous flow from the cartridge;

DESCRIPTION OF THE ILLUSTRATED EMBODIMENT

Figure 1:
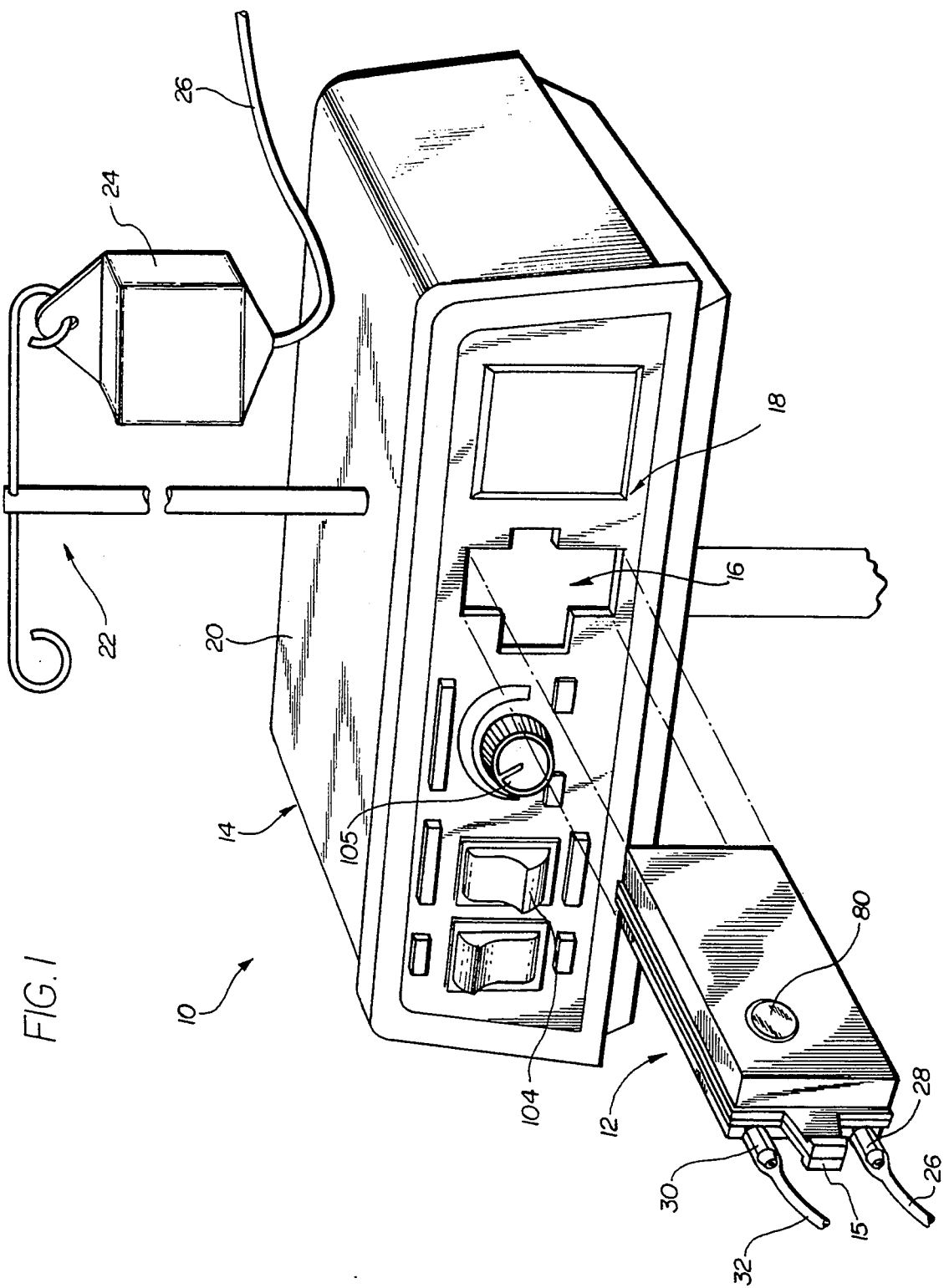
FIG. 1 is a perspective view of one embodiment of a fluid pumping assembly in accordance with the present invention.

Referring to FIG. 1, a fluid pumping system generally designated by reference character 10 is illustrated, in which one embodiment of a pumping cartridge 12 is illustrated in position for installation into system in which cartridge 12 is installed for convenient, single use and removal, and subsequent replacement by a different, sterile cartridge 12. The cartridge 12 is manually inserted or removed from the pump housing 14 through a receptive aperture 16 formed in the face plate 18, and gripped by handle 15. The cover 20 of the pump housing 14 supports a typical hanger 22 on which is hung one or two fluid supply bags 24 containing, for example, sterile saline irrigation solution which is to be pumped by the system 10 for use such as in pressurized surgical irrigation. The delivery tube 26 from the bag 24 is connected to the fluid intake nipple 28 on the cartridge 12. The fluid is pumped and flows through only the cartridge 12, as more fully described hereinafter, so that the pressurized fluid effluent from the cartridge 12 flows from the discharge nipple 30 for delivery through the connected line 32 to the laparoscopic or other surgical instrument (not shown). The fluid flow through cartridge 12 is thus isolated from the remainder of the system 10 which therefore need not be sterilized, and the sterile cartridge 12 maintains sterile condition of the fluid since the convenient installation and removal allow the cartridges 12 to be disposable and a new, sterile cartridge 12 is used for fluid pumping in any subsequent surgical procedure using the system 10.

Figure 2:
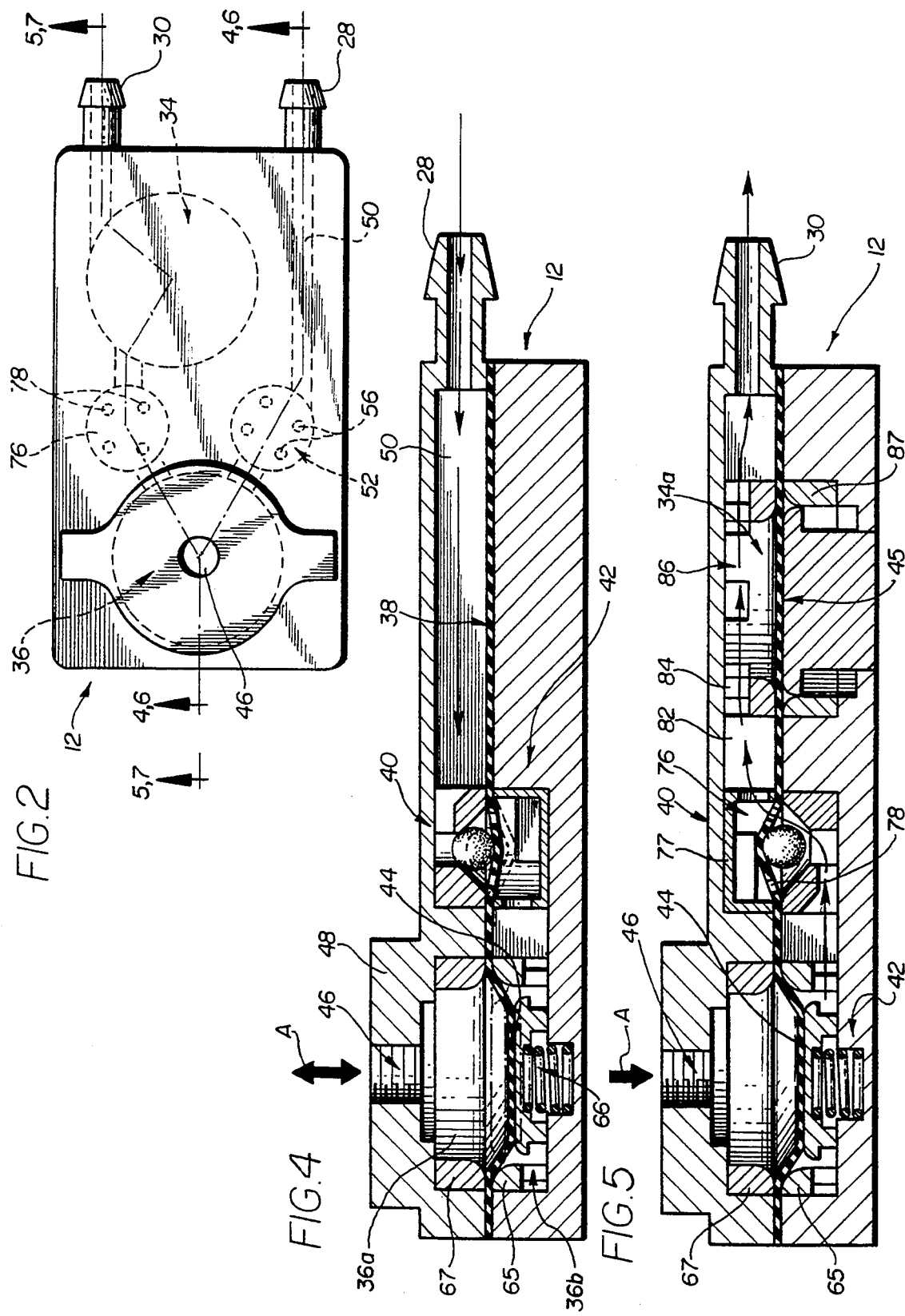
FIG. 2 is a plan view of one embodiment of the pumping cartridge shown in FIG. 1, in accordance with the invention.
Figure 3:
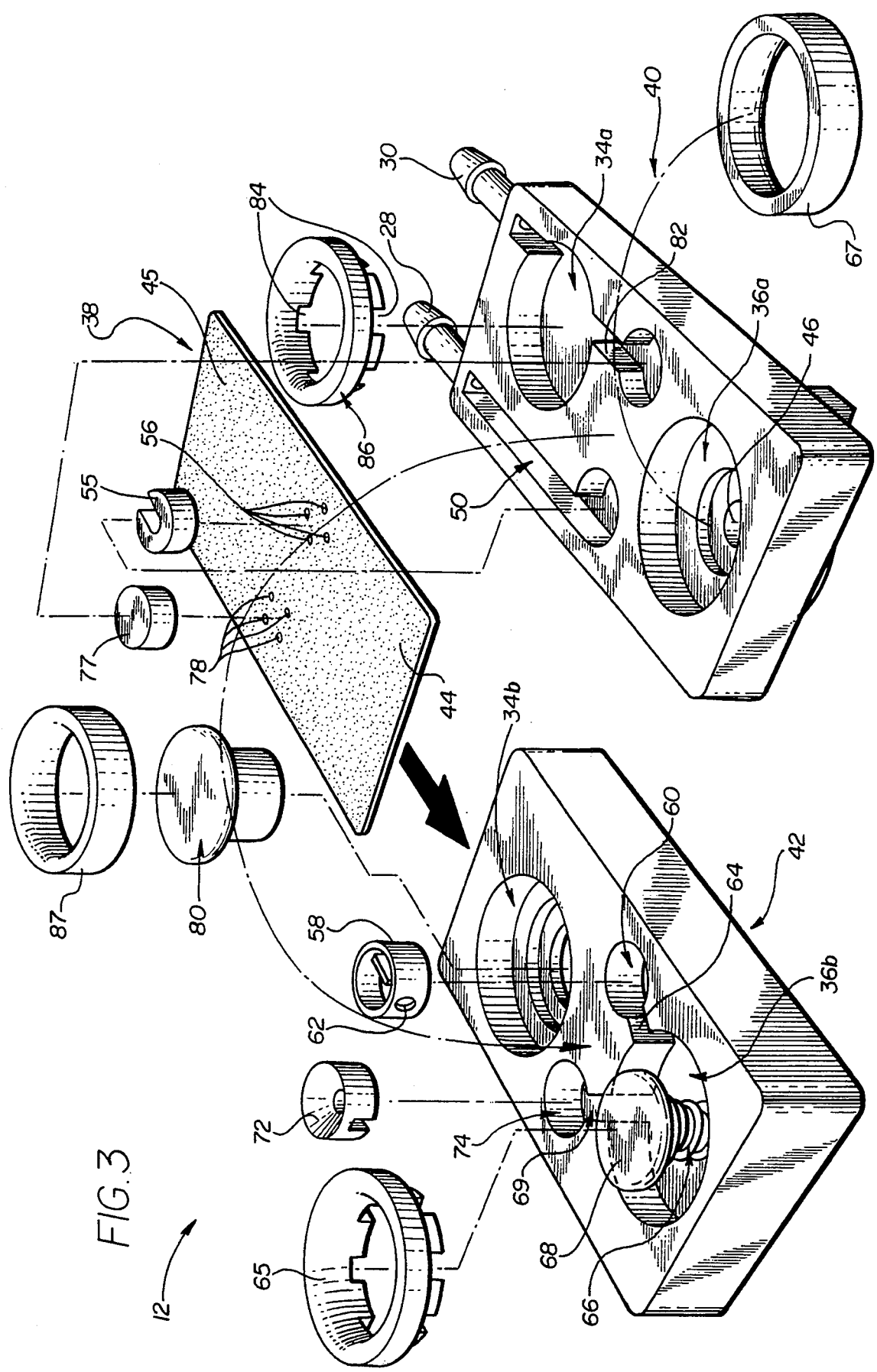
FIG. 3 is an exploded perspective view of the construction of the cartridge shown in FIG. 2.

Referring now to FIGS. 2 and 3, one version or embodiment of a design for cartridge 12 is illustrated, which embodiment provides pumping of the fluid selectively in either a continuous or pulsating flow. The selective pulsating flow is enabled by including in the cartridge 12 an accumulator chamber 34 which receives the pressurized discharge flow from the pump chamber 36. In the illustrated embodiment, the cartridge 12 has a resilient diaphragm 38 of suitable elastomeric material which is retained (by suitable fastening means, not shown) between housing portions or sections generally designated by reference characters 40 and 42. A portion 44 of the diaphragm 38 provides a resilient pump diaphragm which reciprocates within the pumping chamber 36 formed by aligned cylindrical cavities 36a and 36b respectively formed in housing portions 40 and 42. Referring briefly to FIGS. 4 and 5, the reciprocating, pump diaphragm portion 44 is driven by cycled, pneumatic air pressure indicated by arrow A received directly through an air drive conduit 46 which passes through a boss 48 on the wall of the housing portion 40. The air pressure A is cycled by controls more fully described hereinafter.

Referring to FIG. 6, supply fluid is drawn through nipple 28 into the lead conduit 50 from which the flow passes through open intake check valve 52 by dislodgement of the ball 54 from the throat of insert 55 enabling the fluid to pass through the four, through diaphragm apertures 56 (FIGS. 2 and 3). The fluid is drawn through the diaphragm apertures 56 into the intake check valve insert 58 seated within the intake check valve cavity 60 formed in the housing portion 42. The insert 58 has an outlet aperture 62 which leads through the housing channel 64 into the pump cavity 36b to which the flow is drawn by the return stroke of the reciprocating diaphragm pump portion 44 assisted by the expansion of the return spring 66 and flange 68 engaged against the diaphragm portion 44, during the pneumatic exhaust portion of the cycled air drive indicated by arrow B. At the same time, the return stroke of the diaphragm pump portion 44 also draws fluid from channel 69 and closes the ball 70 against the discharge check valve insert 72 seated in the cavity 74 of the housing portion 42. The closure by the check ball 70 causes interruption of flow through the discharge check valve 76 and diaphragm apertures 78, and the resultant reduction of pressure in the accumulator cavity portion 34a produces consequent pulse interruption in the discharge flow from the nipple 30 in the selected pulse flow operation of the cartridge 12.

In the alternative continuous flow (FIG. 8), a selective withdrawal of the accumulator pressure plate 80, controlled as more fully described hereinafter, enables the accumulator diaphragm portion 45 to be resiliently displaced into the accumulator cavity portion 34b within the housing portion 42; when free to displace, the accumulator diaphragm portion 45 will absorb the cycled pulses of increased fluid flow pressure generated by the power stroke of the pump diaphragm portion 44 as shown in FIG. 5. As best viewed in FIG. 5, the power stroke flow uplifts the ball 70 and flows through the discharge check valve 76, diaphragm aperture 78, flow director insert 77, housing channel 82, and flow gap 84 in the accumulator insert 86 as the flow enters the accumulator cavity portion 34a. The accumulator inserts 86 and 87, and the similar pump chamber inserts 65 and 67 provide curved periphery for wear protection of the fixed rim of the diaphragm portions 45 and 44, respectively.

On the return stroke of the pump diaphragm portion 44 as shown in FIG. 7, the accumulator diaphragm portion 45 will resiliently unflex so as to maintain flow pressure on the fluid in the accumulator and prevent any interruption of discharged flow from the nipple 30.

Figure 9:
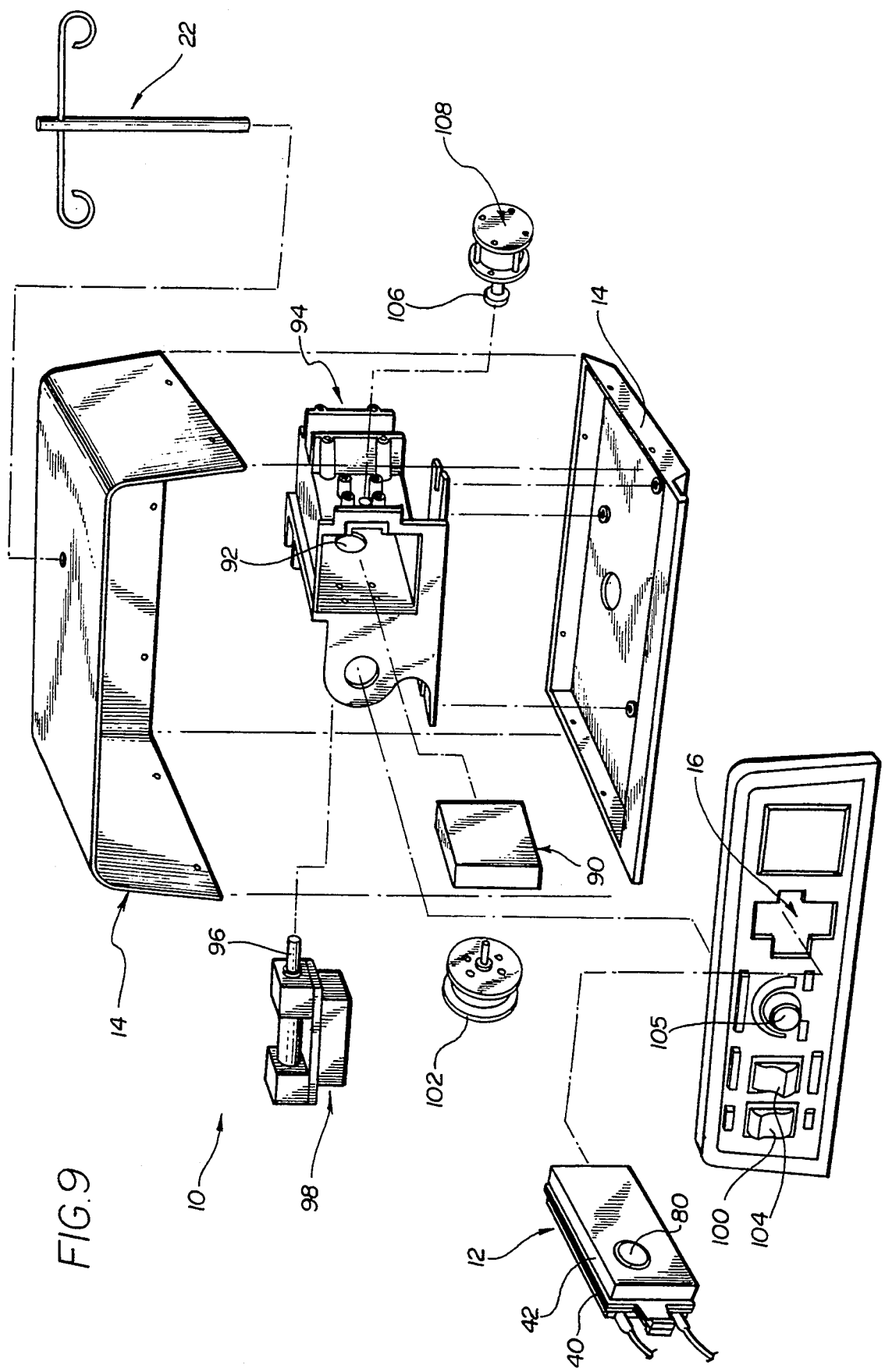
FIG. 9 is an exploded view of the pumping assembly shown in FIG. 1.

Referring now to the illustrated embodiment of the pumping system 10 as shown in FIG. 9, the cartridge 12 is inserted through the face plate aperture 16, into alignment with a clamp platen 90. The clamp platen 90 guides the air drive port 46 of the fully inserted cartridge 12 into alignment with the aperture 92 in support frame 94, which enables the flow connection of the air drive port 46 to the nozzle 96 of the pneumatic pump drive valve 98 which is more fully described hereinafter.

To prepare for pumping operation, an on/off switch 100 will actuate a typical air clamp 102 to press platen 90 and hold a properly inserted cartridge 12 securely in position and seal coupling between the nozzle 96 and air drive port 46 of the cartridge 12. The force exerted by the air clamp 102 also augments the fluid seal of the cartridge housing portions 40 and 42 against the diaphragm 38. Next, the choice of either continuous or pulsed fluid discharge and delivery from the cartridge 12 is controlled by switch 104 which will selectively actuate displacement of a plunger 106 from air cylinder 108 to drive the accumulator pressure plate 80 from the position shown in FIG. 8 to the position shown in FIG. 7 into engagement with the accumulator diaphragm portion 45 which holds it stationary without displacement resulting in pulsating flow from the cartridge 12. The alternative continuous flow operation of the cartridge 12 is controlled by retracting the plunger 106 to allow withdrawal of the accumulator pressure plate 80.

Figure 10:
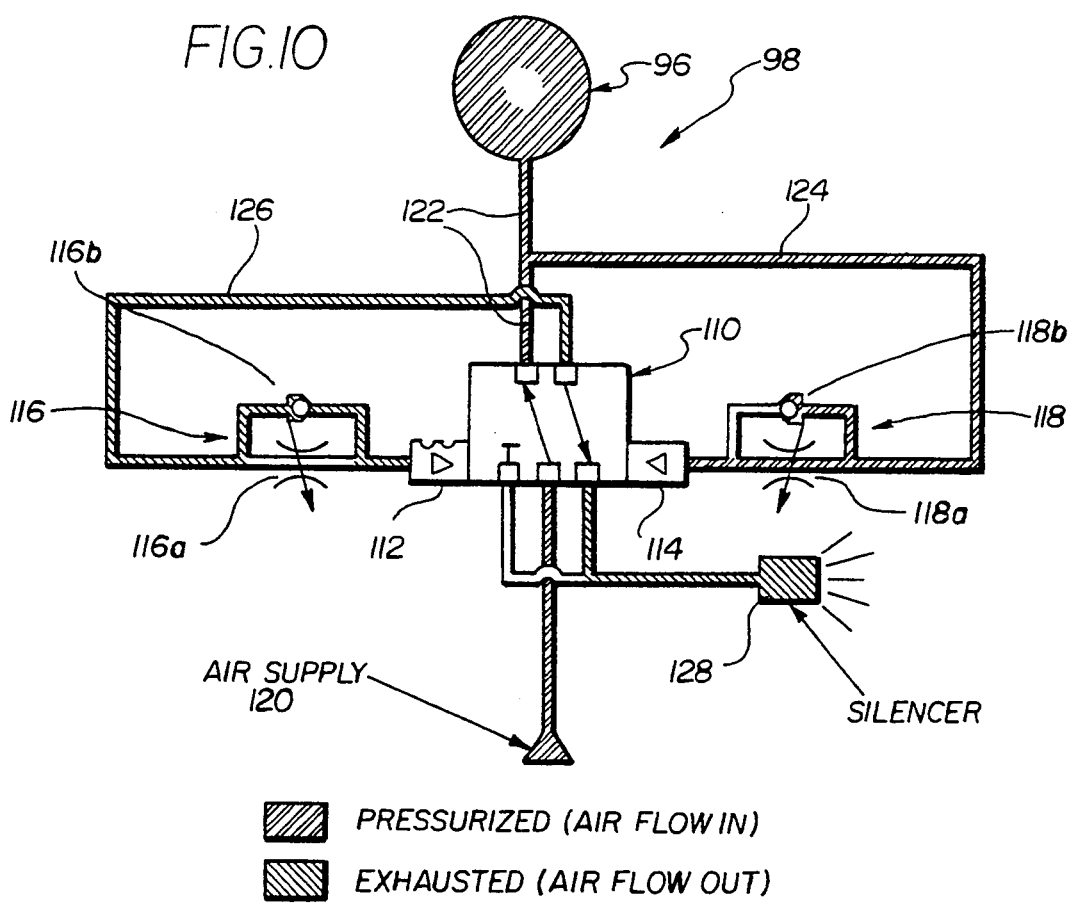
FIGS. 10 and 11 are diagrammatic views of the operation of one embodiment of a pneumatic pump drive valve assembly which controls the cycled pump operation of the illustrated cartridge.
Figure 11:
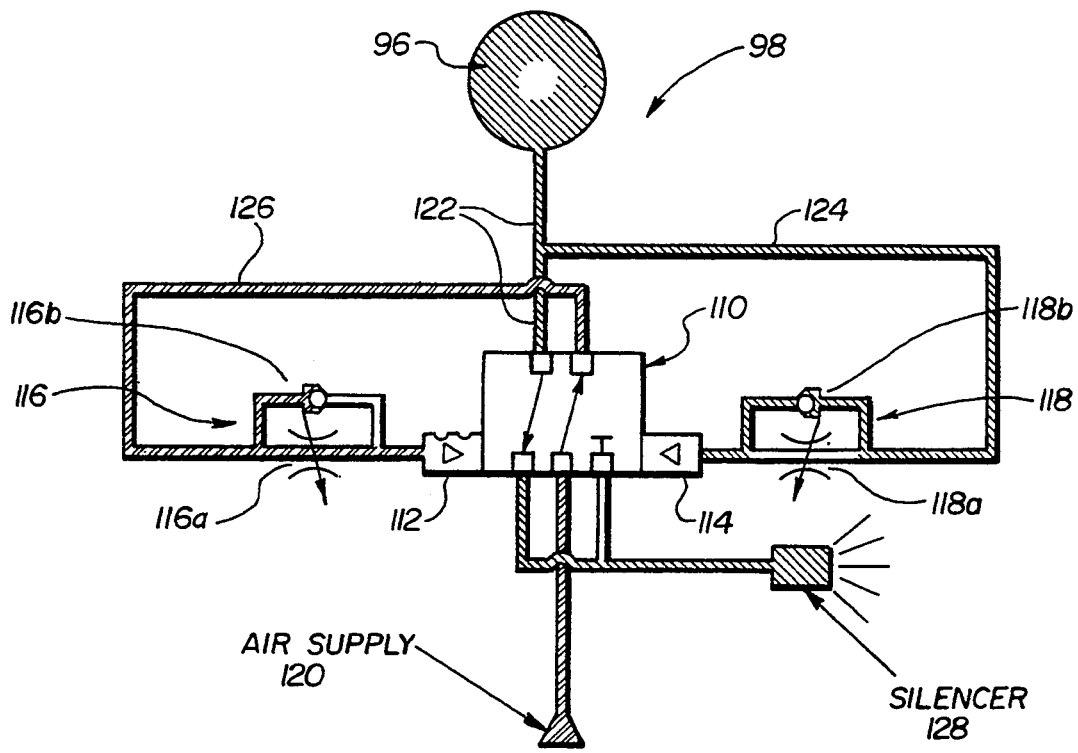

Referring now to FIGS. 10 and 11, the pneumatic pump drive valve assembly 98 includes a two-position, five-port, four-way, detented and air piloted spool valve 110. The valve 110 is shuttled between the two positions by the presence of air pressure at the air pilot ports 112 and 114. The valve pilots are "detented" meaning that the valve will not shuttle until the air pressure is removed from one pilot and made available to the opposite pilot. When pilot 112 senses air pressure, the valve 110 shuttles to the position where the air passage between ports 1 and 2 is open and the air passage between ports 4 and 5 is simultaneously open. When the pilot 114 senses air pressure, the valve 110 shuttles to the position where air passage between ports 1 and 4 is open with simultaneous air passage opening between ports 2 and 3. Flow control valves 116 and 118 are provided to allow for a controlled air flow through respective variable orifice needle valves 116a and 118a in one direction and free flow in the opposite direction via respective internal check valves 116b and 118b.

In operation of the air drive valve assembly 98, the switch 100 activates operation of a pneumatic supply source 120 which also separately supplies (not shown) the air clamp 102 and air cylinder 108, as well as the valve assembly 98. For the power stroke pumping displacement of the cartridge diaphragm portion 44 (FIG. 4) the valve 110 shuttles to communicate the 1-2 position which directs pressurized air through line 122 through nozzle 96 to the cartridge air drive port 46 (FIG. 4). As the power stroke of the diaphragm portion 44 is completed, the resulting back pressure is communicated through line 124 and the needle valve 118a whereupon sufficient pressure triggers the pilot 114. Simultaneously, the pilot 112 is exhausted through the open check valve 116b, through line 126 and through connected ports 4 and 5 of valve 110, discharging through silencer 128 to the atmosphere. Because pilot 112 is exhausted and pilot 114 is pressurized, the spool of valve 110 shuttles to connect ports 1–4 as shown in FIG. 11, to begin the return stroke of the pump diaphragm portion 44 and drawing fluid supply through nipple 28 as shown in FIG. 6.

With the spool of valve 110 connecting ports 1 and 4, the pressurized air from supply 120 is directed through ports 1 and 4 to line 126 while at the same time air is exhausted from cartridge pump cavity 36a through air port 46, nozzle 96, and along line 122 through connected ports 2 and 3 discharging through the silencer 128. Simultaneously, the pilot 114 is exhausted through the open check valve 118b and ports 2 and 3 of valve 110 to the silencer 128. When the pilot 112 is sufficiently pressurized through needle valve 116a from line 126, and pilot 114 exhausted, the valve 110 shuttles to again connect the 1 and 2 ports as shown in FIG. 10 and the succeeding power stroke of the cartridge pump is actuated. Adjustment of the flow control needle valves 116a and 118a, for example by rotary knob 105, enables controlled variation of the cycle rate, so that the valves 116a and 118a also function as timers for the cycled cartridge pump operation, particularly to enable variation in the pulsation frequency when pulse flow of irrigation fluid is selected.

With the exception of a conventionally, electrically powered air supply, the illustrated embodiment of the pumping system 10 is entirely pneumatic. Electrically operated components, such as pump drive and accumulator control, are optional modifications as well as a rotary pump in the cartridge coordinated with a selectively oscillating accumulator to produce pulse flow. Accordingly, particular embodiments of the present invention have been described herein while it will be obvious to those skilled in the art that changes and modifications in various aspects may be made without departing from the broad scope of the invention. Consequently, the scope of the invention is not limited by any particular embodiment but is defined by the appended claims and the equivalents thereof.

The invention is claimed as follows:

1. A fluid pumping cartridge for particular use in a single surgical procedure in order to deliver and maintain sterile condition of the pumped fluid, comprising: a pumping chamber formed in a cartridge housing adapted for replaceable connection to and disconnection from a pump control structure; and pump means integrally contained in said cartridge housing arranged for pumping sterile fluid from said pumping chamber and adapted for connection to a pump drive structure provided by said pump control structure, in order to pump said sterile fluid through said pumping cartridge flowing entirely isolated from the pump control structure and to ensure that the fluid is maintained sterile during said pumping and a pulsation controlling, accumulator chamber in flow communication with said pump means, said accumulator chamber having a deflectable diaphragm defining one wall thereof; and pulsation control means for selectively enabling said diaphragm to oscillate and absorb fluid flow pulses pumped from said pump means in order to produce selectively continuous flow of said fluid from said cartridge.

2. A pumping cartridge according to claim 1 wherein said pumping means comprises a diaphragm member resiliently reciprocating within said pumping chamber to produce said pumping.

3. A pumping cartridge according to claim 1 wherein said pumping means diaphragm member and said accumulator chamber displaceable diaphragm are formed as respective first and second portions of an integral diaphragm structure.

4. A pumping cartridge according to claim 3 further comprising check valve means for controlling one-way flow from said pumping chamber to said accumulator chamber, wherein said check valve means includes at least one flow aperture through said integral diaphragm structure.

5. A pumping cartridge according to claim 1 further comprising check valve means for controlling one-way fluid flow through said cartridge.

6. A pumping cartridge according to claim 1 wherein said accumulator chamber includes selectively displaceable diaphragm to enable selectively variable volume of said accumulator chamber, said cartridge further comprising fixing means for selectively preventing displacement of said diaphragm in order to selectively fix volume of said accumulator chamber.

7. A pumping cartridge according to claim 6 wherein said fixing means comprises a holding member selectively movable into fixing engagement with said diaphragm.

8. A fluid pumping cartridge for particular use in a single surgical procedure in order to deliver and maintain sterile condition of the pumped fluid, comprising: a pumping chamber formed in a cartridge housing adapted for manually replaceable connection to and disconnection from a pump control structure; and pump means integrally contained in said cartridge housing arranged for pumping sterile fluid from said pumping chamber and adapted for connection to a pump drive structure provided by said pump control structure, wherein said pump means comprises a resilient diaphragm member clamped between first and second portions of said cartridge housing, said cartridge further comprising a pulsation controlling accumulator chamber including a selectively displaceable diaphragm defining one wall thereof which is capable of selective oscillation and absorption of fluid flow pulses driven by said pump drive structure in order to produce selectively continuous flow of said sterile fluid from said accumulator chamber and cartridge.

9. A pumping cartridge according to claim 8 wherein said pumping chamber comprises first and second cavity portions respectively formed within said first and second housing portions between which said diaphragm member resiliently oscillates to produce said pumping.

10. A pumping cartridge according to claim 9 wherein said cartridge further integrally comprises pulsation control means for selectively discharging said fluid from said cartridge in either a continuous flow or pulsating flow of said fluid.

11. A pumping cartridge according to claim 10 further comprising check valve means for controlling one-way flow from said pumping chamber to said accumulator chamber.

12. A pumping cartridge according to claim 8 wherein said accumulator chamber is defined by first and second accumulator cavity portions respectively formed in said first and second housing portions wherein said displaceable diaphragm is clamped between said accumulator cavity portions.

13. A pumping cartridge according to claim 8 further comprising check valve means for controlling one-way flow from said pumping chamber.

14. A fluid pumping cartridge for particular use in a single surgical procedure in order to deliver and maintain sterile condition of the pumped fluid, comprising: a pumping chamber formed in a cartridge housing adapted for replaceable connection to and disconnection from a pump control structure, and an accumulator chamber in flow communication with said pumping chamber, wherein said cartridge housing comprises first and second housing portions, between said housing portions is clamped an integral diaphragm structure including a first diaphragm portion resiliently oscillating within said pumping chamber to produce said pumping action, and a second diaphragm portion forming at least one wall of said accumulator chamber which is selectively displaceable to enable selectively variable volume of said accumulator chamber in order to generate selective discharge of said fluid from said cartridge in either a continuous flow or pulsating flow of said fluid.

15. A fluid pumping assembly for particular use in surgical procedures in order to deliver and maintain sterile condition of a pumped fluid, comprising in combination a pump control structure and a replaceable pump cartridge, such that said pump control structure is designed to have the fluid pump cartridge connected and disconnected thereto, to enable convenient replacement thereof; said pump control structure including a pump drive means; said pump cartridge containing fluid pump means adapted for connection to said pump drive structure, in order to pump sterile fluid through said pumping cartridge flowing entirely isolated from said pump control structure to ensure that said fluid is maintained sterile during said pumping action, and a pulsation controlling accumulator chamber including a selectively deflectable diaphragm defining one wall thereof which is capable of selective oscillation and absorption of fluid flow pulses driven by said pump drive structure in order to produce selectively continuous flow of said sterile fluid from said accumulator chamber and cartridge.

16. A pumping assembly according to claim 15 wherein said pump control structure further comprises clamp means for clamping said connected cartridge and for enabling and disabling pumping actuation thereof.

17. A pumping assembly according to claim 15 wherein said pump drive means comprises a pneumatic driving system adapted for powering said cartridge pump means.

18. A pumping assembly according to claim 17 wherein said cartridge pump means comprises a reciprocating pumping element.

19. A pumping assembly according to claim 18 wherein said pneumatic drive system is adapted to generate cycled, alternating air pressure and exhaust communication with said reciprocating pumping element.

20. A pumping assembly according to claim 19 wherein said pneumatic drive system comprises pneumatic valve means for cycled switching of supplied air pressure into and out of communication with said reciprocating pumping element.

21. A pumping assembly according to claim 20 wherein said valve means comprises a valve element adapted for oscillating motion to establish said cycled air communication.

22. A pumping assembly according to claim 21 wherein said pneumatic drive system further comprises a conduit providing said communication with said pumping element, and wherein said valve element oscillates between a first position connecting said conduit to a pneumatic supply source, and a second position exhausting said conduit.

23. A pumping assembly according to claim 15 further comprising fixing means for selectively preventing displacement of said diaphragm in order to selectively fix volume of said accumulator chamber.

24. A pumping assembly according to claim 23 wherein said fixing means comprises a holding member formed in said cartridge and selectively movable into engagement with said diaphragm to prevent said displacement thereof.

25. A pumping assembly according to claim 24 further comprising drive means for selectively driving and maintaining said engagement by said holding member.

26. A fluid pumping assembly for particular use in surgical procedures in order to deliver and maintain sterile condition of a pumped fluid, comprising in combination a pump control structure and a replaceable pump cartridge, such that said pump control structure is designed to have the fluid pump cartridge connected and disconnected thereto, to enable convenient replacement thereof; said pump control structure including a pump drive means; said pump cartridge containing fluid pump means adapted for connection to said pump drive structure, in order to pump sterile fluid through said pumping cartridge flowing entirely isolated from said pump control structure to ensure that said fluid is maintained sterile during said pumping action, wherein said pump drive means comprises a pneumatic driving system adapted for powering said cartridge pump means including a reciprocating pumping element, and wherein said pneumatic drive system is adapted to generate cycled, alternating air pressure and exhaust communication with said reciprocating pumping element, said pneumatic drive system comprising pneumatic valve means for cycled switching of supplied air pressure into and out of communication with said reciprocating pumping element and said valve means comprises a valve element adapted for oscillating motion to establish said cycled air communication, said pneumatic drive system further comprising a conduit providing said communication with said pumping element, said valve element oscillating between a first position connecting said conduit to a pneumatic supply source and a second position exhausting said conduit and, said valve means further comprises first and second pilot means for controlling said oscillation of said valve element.

27. A pumping assembly according to claim 26 wherein motion of said valve element is triggered by pneumatic trigger pressure in one of said pilot means together with discontinued pneumatic pressure in said other pilot means.

28. A pumping assembly according to claim 26 wherein said first position of said valve element additionally establishes communication of pressure from said source through a branch circuit from said conduit to said first pilot means, and said first position additionally establishes separate flow communication through a separate pneumatic circuit from said second pilot means to a separate flow channel through said valve means communicating to exhaust discharge therefrom, said second position of said valve element additionally communicating pneumatic pressure from said source through said separate circuit to said second pilot means in addition to communicating exhaust flow from said conduit and branch circuit to exhaust discharge from said valve means.

29. A pumping assembly according to claim 28 wherein each of said branch and separate circuits comprises an adjustable control valve controlling flow to said respective pilot means to enable adjustment of frequency of said oscillating motion and reciprocation of said pumping element.

30. A pumping assembly according to claim 26 further comprising first and second adjustable control valves controlling pneumatic flow respectively through said first and second pilot means in order to enable adjustable frequency of said oscillating motion of said valve element and reciprocation of said pumping element.

31. A cartridge for particular use in a single surgical procedure in order to deliver and maintain sterile condition of the pumped fluid, comprising:
a cartridge housing adapted for replaceable connection to a pump control structure in order to isolate therefrom pumping of sterile fluid through the cartridge; and
a pulsation controlling, accumulator chamber including a deflectable diaphragm defining one wall thereof which is capable of oscillation and absorption of pumped fluid flow pulses in order to produce continuous flow of said sterile fluid from said accumulator chamber and cartridge.

32. A cartridge according to claim 31 further comprising fixing means for selectively preventing displacement of said diaphragm in order to selectively transmit said fluid flow pulses through said accumulator chamber for discharge of said fluid pulses from said cartridge.

33. A cartridge according to claim 31 wherein said fixing means comprises a holding member formed in said cartridge and selectively movable into engagement with said diaphragm to prevent said selective oscillation thereof.

34. A cartridge according to claim 31 further comprising pump means integrally contained in said cartridge housing and arranged for pumping said sterile fluid into said accumulator chamber and adapted for connection to a pump drive structure provided by said pump control structure.

35. A cartridge according to claim 34 wherein said pump means comprises a diaphragm member resiliently reciprocating within a pumping chamber formed in said cartridge.

36. A cartridge according to claim 35 wherein said pump means diaphragm member and said accumulator chamber diaphragm are formed as respective first and second portions of an integral diaphragm structure.

37. A fluid pumping cartridge for particular use in a single surgical procedure in order to deliver and maintain sterile condition of the pumped fluid, comprising:
a pump means integrally arranged within a cartridge housing adapted for replaceable connection to a pump drive structure in order to isolate from the pump drive structure, pumping of sterile fluid through the cartridge; and a pulsation controlling, accumulator chamber in flow communication with said pump means, said accumulator chamber having a diaphragm defining one wall thereof and pulsation control means for selectively enabling said diaphragm to oscillate and absorb fluid flow pulses pumped from said pump means and to selectively produce continuous flow of said fluid from said cartridge.

38. A cartridge for particular use in a single surgical procedure in order to deliver and maintain sterile condition of pumped surgical fluid, comprising:
a cartridge housing a pulsation controlling, accumulator chamber including a deflectable diaphragm defining one wall thereof which is capable of oscillation and absorption of pumped fluid flow pulses in order to produce continuous flow of said sterile fluid from said accumulator chamber and cartridge.

39. A cartridge according to claim 38, wherein said deflectable diaphragm has sufficient resilience to maintain a flow pressure on said fluid in said accumulator chamber.

* * * * *